United States Patent
Ekambaram et al.

(10) Patent No.: US 10,144,712 B2
(45) Date of Patent: Dec. 4, 2018

(54) QUINOLINES AND PROCESS FOR THE PREPARATION THEREOF

(71) Applicant: Council of Scientific and Industrial Research, New Delhi (IN)

(72) Inventors: Balaraman Ekambaram, Pune (IN); Vinod Gokulkrishna Landge, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/543,714

(22) PCT Filed: Jan. 15, 2016

(86) PCT No.: PCT/IN2016/050014
§ 371 (c)(1),
(2) Date: Jul. 14, 2017

(87) PCT Pub. No.: WO2016/113759
PCT Pub. Date: Jul. 21, 2016

(65) Prior Publication Data
US 2018/0009759 A1    Jan. 11, 2018

(30) Foreign Application Priority Data
Jan. 15, 2015 (IN) .............. 0127/DEL/2015

(51) Int. Cl.
| | |
|---|---|
| C07D 215/38 | (2006.01) |
| C07D 215/04 | (2006.01) |
| C07D 215/12 | (2006.01) |
| C07D 215/18 | (2006.01) |
| C07D 215/20 | (2006.01) |
| B01J 31/04 | (2006.01) |
| B01J 31/18 | (2006.01) |

(52) U.S. Cl.
CPC ............ C07D 215/38 (2013.01); B01J 31/04 (2013.01); B01J 31/181 (2013.01); C07D 215/04 (2013.01); C07D 215/12 (2013.01); C07D 215/18 (2013.01); C07D 215/20 (2013.01)

(58) Field of Classification Search
CPC .. C07D 215/38; C07D 215/20; C07D 215/18; C07D 215/04; C07D 215/12; B01J 31/04; B01J 31/181
See application file for complete search history.

(56) References Cited

PUBLICATIONS

Liu, Agnew Chem vol. 126, 4275-4279, 2014. (Year: 2014).*
Landge, Int J Inorg Organometallic and Bioinorganic Chemistry, 44(35), 15382-15386, 2015. (Year: 2015).*
Ano, J Ann Chem Soc, 133, 12984-102986, 2011. (Year: 2011).*
Landge et al., "Well-defined palladium(II) complexes for ligand-enabled C(sp3)-alkynylation", Dalton Transactions: The International Journal for Inorganic, Organometallic and Bioinorganic Chemistry, Jul. 22, 2015, pp. 15382-15386, vol. 44, No. 35.
Staubitz et al., "Expeditious Functionalization of Quinolines in Positions 2 and 8 via Polyfunctional Aryl- and Heteroarylmagnesium Intermediates", Synthesis, Jan. 1, 2003, pp. 233-242, No. 2.
Liu et al., "Rhodium(III)-Catalyzed Alkenylation Reactions of 8-Methylquinolines with Alkynes by C(sp3)-H Activation", Angewandte Chemie, Apr. 14, 2014, pp. 4275-4279, vol. 126, No. 16.
Ano et al., "Palladium-Catalyzed Direct Ethynylation of C(sp3)-H Bonds in Aliphatic Carboxylic Acid Derivatives", Journal of the American Chemical Society, Aug. 24, 2011, pp. 12984-12986, vol. 133, No. 33.

* cited by examiner

Primary Examiner — D Margaret M Seaman
(74) Attorney, Agent, or Firm — Carmody Torrance Sandak & Hennessey LLP

(57) ABSTRACT

The present invention discloses novel N-Heterocyclic compounds of formula A, [Formula A] And a ligand-enabled palladium-catalyzed process for preparation of novel N-Heterocyclic compounds of Formula A via C—H alkynylation of N-heterocycles with alkynyl halides.

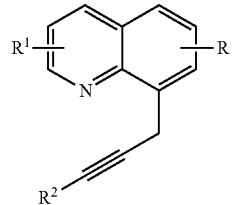

Formula A

4 Claims, 2 Drawing Sheets

QUINOLINES AND PROCESS FOR THE PREPARATION THEREOF

FIELD OF THE INVENTION

The present invention relates to an N-Heterocyclic compound of formula A.

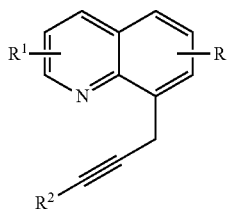

Formula A

Particularly, the present invention relates to a process for the preparation of N-Heterocyclic compound of formula A. More particularly, present invention relates to N-Heterocyclic compound of formula A useful for ligand synthesis in transition-metal catalysis.

BACKGROUND AND PRIOR ART OF THE INVENTION

Alkynes are very important building blocks in synthetic chemistry and in material science and they are also a common motif in pharmaceuticals. The unique physical properties of alkynes (rigid structure and conjugating π system) make them an attractive functional group for unsaturated molecular scaffolds. Because of their unsaturated, high-energy structure further derivatization in many synthetic transformations (including cycloaddition, metathesis, click reaction etc.) may be possible and leads to various useful molecules.

The development of catalytic system for direct conversion of inert C—H bonds into C-alkynyl bonds is very attractive, simplest and sustainable method as the alkyne moiety is of significant importance for various organic transformations including cycloaddition, metathesis, click reaction etc. In addition alkynes are outstanding building blocks in synthetic chemistry and in material science and they are also a common motif in drugs. Because of the susceptibility of terminal alkynes to homocoupling under the commonly employed oxidative reaction conditions, C—H alkynylation is largely underexplored.

Catalysts based direct activation of C—H bonds provides a sustainable and an atom-economical synthetic strategy to diverse organic molecules from simple, pre-functionalized substrates. The selection of ligands is very crucial in the design of such active catalytic systems. Ligands would alter the electronic and steric properties of the active catalyst and thus they could significantly accelerate C—H activation and successive bond forming reactions. Although, ligand-enabled C(sp$^3$)-H activation has emerged as a powerful tool for rapid, straightforward construction of the carbon-carbon and the carbon-heteroatom bonds, there still remains a significant challenge in the field of C(sp$^3$)-H activation.

Article titled "Rhodium(III)-catalyzed alkenylation reactions of 8-methylquinolines with alkynes by C(sp$^3$)-H activation" by B Liu et al. published in Angew Chem. Int Ed Engl., 2014; 53(16), pp 4191-4195 reports alkenylation reactions of 8-methylquinolines with alkynes, catalyzed by [{Cp*RhCl$_2$}$_2$], proceeds efficiently to give 8-allylquinolines in good yields by C(sp$^3$)-H bond activation. These reactions are highly regio- and stereoselective.

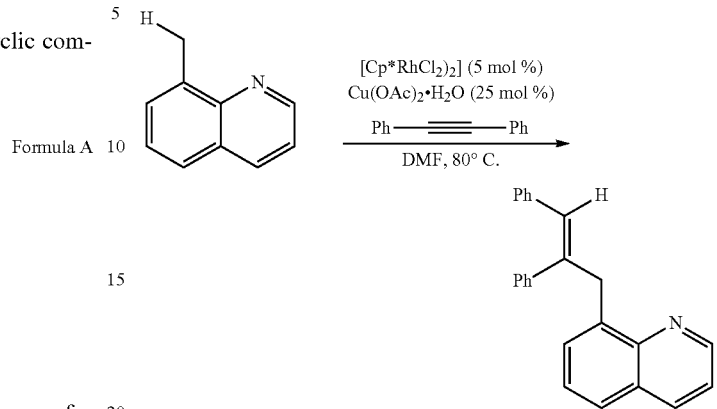

Article titled "Palladium-Catalyzed Direct Ethynylation of C(sp$^3$)-H Bonds in Aliphatic Carboxylic Acid Derivatives" by Y Ano et al. published in J. Am. Chem. Soc., 2011, 133 (33), pp 12984-12986 reports first catalytic alkynylation of unactivated C(sp$^3$)-H bonds by straightforward introduction of an ethynyl group into aliphatic acid derivatives under palladium catalysis. This new reaction can be applied to the rapid elaboration of complex aliphatic acids, for example, via azide/alkyne cycloaddition.

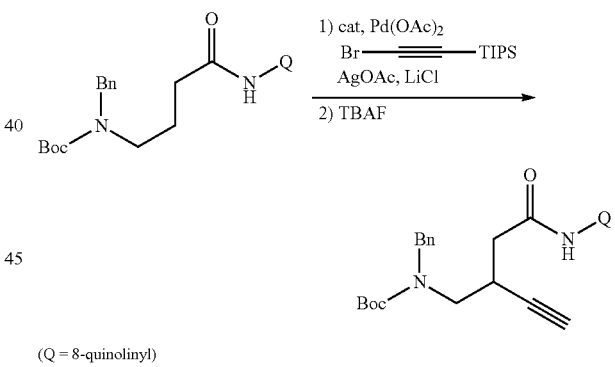

(Q = 8-quinolinyl)

Article titled "Palladium(0)-Catalyzed Alkynylation of C(sp$^3$)-H Bonds" by J He et al. published in J. Am. Chem. Soc., 2013, 135 (9), pp 3387-3390 reports alkynylation of β-C(sp$^3$)-H bonds in aliphatic amides with alkynyl halides enabled using Pd(0)/N-heterocyclic carbene (NHC) and Pd(0)/phosphine (PR$_3$) catalysts.

Article titled "Direct palladium-catalyzed C-3 alkynylation of indoles" by Y Gu et al. published in Tetrahedron Letters, 2009, 50 (7), pp 763-766 reports direct palladium-catalyzed coupling reaction of indoles with alkynyl bromides In the presence of catalytic amount of PdCl$_2$(PPh$_3$)$_2$ and 2.0 equiv. NaOAc, the coupling reaction of indoles with alkynyl bromides proceeded smoothly at 50° C. to give the corresponding 3-alkynylindoles with high regioselectivity in good to excellent yields.

US 10,144,712 B2

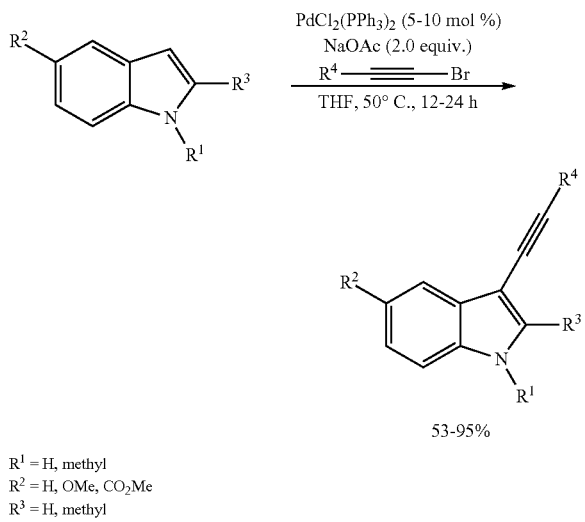

R[1] = H, methyl
R[2] = H, OMe, CO$_2$Me
R[3] = H, methyl

Article titled "Direct Palladium-Catalyzed Alkynylation of N-Fused Heterocycles" by N Seregin et al. published in *J. Am. Chem. Soc.*, 2007, 129 (25), pp 7742-7743 reports direct C—H alkynylation of electron-rich heteroaromatics. This mild, simple, and general method allows for the efficient synthesis of diverse alkynyl heterocycles.

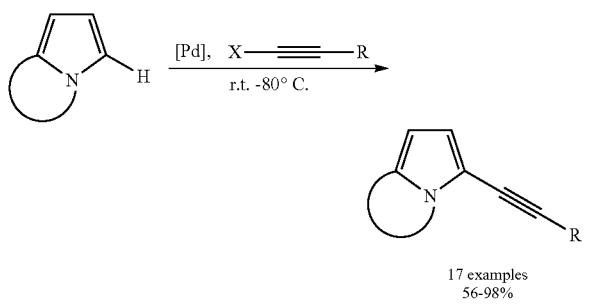

17 examples
56-98%

Article titled "Catalytic Coupling of C—H and C—I Bonds Using Pyridine As a Directing Group" by D Shabashov et al. published in *Org. Lett.*, 2005, 7 (17), pp 3657-3659 reports a method for the palladium-catalyzed arylation of pyridines and pyrazoles. Both aliphatic and aromatic C—H bonds may be functionalized using this method. A bromo substituent is tolerated on the aryl iodide coupling component.

The prior art reports C—H alkynylation of aliphatic carboxylic acid derivatives using template strategy. Due to cyclometalation ability of 8-methylquinoline several transition-metal-catalyzed C(sp$^3$)-H bond activation of 8-methylquinoline has been reported by various research groups. Despite a number of reports concerning C(sp$^2$)-H alkynylation reactions, methods to convert C(sp$^3$)-H bonds to C(sp$^3$)-alkynyl bonds remain extremely rare. Accordingly, the present invention provides efficient C—H alkynylation of inert C(sp$^3$)-H bonds of N-heterocycles.

The main objective of the present invention is to provide N-heterocyclic compounds of formula A.

Another objective of the present invention is to provide a process for the preparation of N-heterocyclic compounds of formula A.

Yet another objective of the present invention is to provide N-heterocyclic compounds of formula A useful for ligand synthesis in transition-metal catalysis.

Yet another objective of the present invention is to provide a ligand-enabled palladium-catalyzed straightforward and efficient C—H alkynylation of inert C(sp$^3$)-H bonds of N-heterocycles (quinoline and pyridine derivatives) using a chelation-assisted strategy.

SUMMARY OF THE INVENTION

Figure 1A:
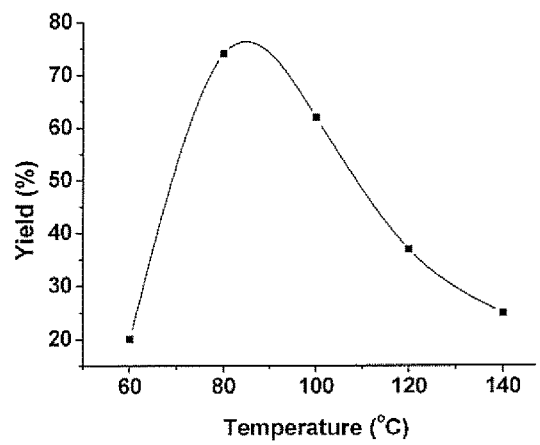
FIG. 1A and FIG. 1B represent effect of temperature and reaction time respectively for the C—H alkynylation of inert C(sp$^3$)-H bonds of N-heterocycles (in particular quinolines).

Accordingly, present invention provides a heterocyclic compound of formula A

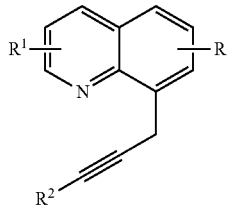

Formula A wherein,
R[1] is independently selected from the group consisting of hydrogen, alkyl (linear and branched), cycloalkyl, aryl, heterocyclyl, heteroaryl, alkylcycloalkyl, alkylaryl, alkylheterocyclyl, alkylheteroaryl, alkenyl, halogen, trifluromethyl, nitro, amide, ester, cyano, alkoxy, alkylamino, arylamino, an inorganic support and a polymeric moiety;
R is selected from the group consisting of H, alkyl (linear, branched), cycloalkyl, ring which may be further substituted and selected from the group consisting of alkyl (linear and branched), cycloalkyl, aryl, heterocyclyl, heteroaryl, alkylcycloalkyl, alkylaryl, alkylheterocyclyl, alkylheteroaryl, alkenyl, halogen, triflurometyl, nitro, amide, ester (—CO$_2$R[1], —OC(O)R[1], —OC(O)CF$_3$, —OSO$_2$R[1], —OSO$_2$CF$_3$) cyano, alkoxy, alkylamino (mono or di), arylamino (mono or di), —SR', an inorganic support and a polymeric moiety;
R[2] is selected from the group consisting of H and TIPS group.

In an embodiment of the present invention, representative compound of formula 1 comprising:
8-(3-(triisopropylsilyl)prop-2-ynyl)quinoline (3a);
5-methoxy-8-(3-(triisopropylsilyl)prop-2-ynyl)quinoline (3b);
N,N-dimethyl-8-(3-(triisopropylsilyl)prop-2-ynyl)quinolin-5-amine (3c);
5-methyl-8-(3-(triisopropylsilyl)prop-2-ynyl)quinoline (3d);
(E)-5-styryl-8-(3-(triisopropylsilyl)prop-2-ynyl)quinoline (3e);

5-fluoro-8-(3-(triisopropylsilyl)prop-2-ynyl)quinoline (3f);
5-bromo-8-(3-(triisopropylsilyl)prop-2-ynyl)quinoline (3g);
5-(trifluoromethyl)-8-(3-(triisopropylsilyl)prop-2-ynyl)quinoline (3h);
5-nitro-8-(3-(triisopropylsilyl)prop-2-ynyl)quinoline (3i);
7-methyl-8-(3-(triisopropylsilyl)prop-2-ynyl)quinoline (3j);
7-fluoro-8-(3-(triisopropylsilyl)prop-2-ynyl)quinoline (3k);
7-chloro-8-(3-(triisopropylsilyl)prop-2-ynyl)quinoline (3l);
6-methyl-8-(3-(triisopropylsilyl)prop-2-ynyl)quinoline (3m);
6-chloro-8-(3-(triisopropylsilyl)prop-2-ynyl)quinoline (3n);
4-chloro-8-(3-(triisopropylsilyl)prop-2-ynyl)quinoline (3o), and
ethyl 4-chloro-8-(3-(triisopropylsilyl)prop-2-ynyl)quinoline-3-carboxylate (3p);
8-(prop-2-yn-1-yl)quinoline. (4a).

In an embodiment, present invention provides a process for preparation of heterocyclic compound of formula A comprising the steps of:
 a) stirring the reaction mixture of alkynyl halide (2), 8-methylquinolines (1a-1p), Palladium-complex, ligand, oxidant, and solvent for the period in the range of 2 to 12 hrs at temperature in the range of 60° C. to 140° C. to afford alkynylated product 3a-p of formula A (wherein $R^2$ is TIPS);
 b) adding Tetra-n-butylammonium fluoride (TBAF) in THF to the alkynylated product of step (a) and diluting the mixture with tetrahydrofurane (THF) followed by stirring the reaction mixture at room temperature in the range of 20 to 30° C. for a period in the range of 1 to 2 hr to afford desired desilated product of formula A, where in $R^2$ is H.

In another embodiment of the present invention, said ligand is selected from is selected from the group consisting of 1,10-phenonthroline, 4-4dimethoxy-2,2-bipyridine, 4,4'-dimethyl-2,2'-dipyridyl, 2,6-Pyridinedicarboxylic acid, Chelidamic acid, 2,2'-Bipyridyl, 3,4,7,8-Tetramethyl-1,10-phenanthroline, 4,7-Dimethoxy-1,10-phenanthroline, L-Isoleucine, 2,6-Pyridinedimethanol, 4-Hydroxy-2,6-Pyridinedicarboxylic acid, 2-Picolinic acid, 2,6-Lutidine, 2,4,6-Trimethylpyridine, 2,6-Di-tert-butylpyridine, 2-Methylpyridine.

In yet another embodiment of the present invention, said oxidant is selected from the group consisting of potassium persulfate ($K_2S_2O_8$), Oxygen ($O_2$), Copper(II) acetate [Cu(OAc)$_2$], Copper (II) triflate [Cu(OTf)$_2$], manganese(III) acetate [Mn(OAc)$_3$.2H$_2$O], sodium periodate (NaIO$_4$), N-Methylmorpholine N-oxide (NMO), 1,4-Benzoquinone (BQ), (Diacetoxyiodo)benzene, silver carbonate, silver acetate and silver oxide (Ag$_2$O).

In yet another embodiment of the present invention, said alkynyl halide is (bromoethynyl) triisopropylsilane.

In yet another embodiment of the present invention, said solvent is selected from the group consisting of 1,2-dichloroethane (DCE), arenes, toluene, o-xylene, chlorobenzene (PhCl), Dimethylformamide (DMF), Dimethyl sulfoxide (DMSO), Dimethylacetamide (DMA), Dioxane, tetrahydrofuran (THF) and trifluoroethanol (CF$_3$CH$_2$OH).

In yet another embodiment of the present invention, said process is carried out at argon or nitrogen atmosphere.

In yet another embodiment of the present invention, said compound is useful for ligand synthesis in transition-metal catalysis.

DETAIL DESCRIPTION OF THE INVENTION

Present invention provides a compound of formula A

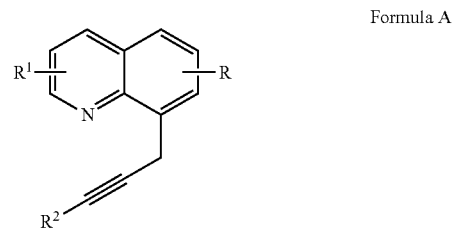

Formula A wherein
$R^1$ is independently selected from hydrogen, alkyl (C1-C6) (linear and branched), cycloalkyl, aryl, heterocyclyl, heteroaryl, alkylcycloalkyl, alkylaryl, alkylheterocyclyl, alkylheteroaryl, alkenyl, halogen, triflurometyl, nitro, amide, ester, cyano, alkoxy, alkylamino, arylamino, an inorganic support or a polymeric moiety;
R is selected from the group consisting of H, alkyl (linear, branched), cycloalkyl, ring which may be further substituted and selected from the group consisting of alkyl (linear and branched), cycloalkyl, aryl, heterocyclyl, heteroaryl, alkylcycloalkyl, alkylaryl, alkylheterocyclyl, alkylheteroaryl, alkenyl, halogen, triflurometyl, nitro, amide, ester (—CO$_2$R$^1$, —OC(O)R$^1$, —OC(O)CF$_3$, —OSO$_2$R', —OSO$_2$CF$_3$) cyano, alkoxy, alkylamino (mono or di), arylamino (mono or di), —SR$^1$, an inorganic support or a polymeric moiety.
$R^2$ is selected from the group consisting of H and TIPS group.

Representative compound of formula A are as follows:
8-(3-(triisopropylsilyl)prop-2-ynyl)quinoline (3a);
5-methoxy-8-(3-(triisopropylsilyl)prop-2-ynyl)quinoline (3b);
N,N-dimethyl-8-(3-(triisopropylsilyl)prop-2-ynyl)quinolin-5-amine (3c);
5-methyl-8-(3-(triisopropylsilyl)prop-2-ynyl)quinoline (3d);
(E)-5-styryl-8-(3-(triisopropylsilyl)prop-2-ynyl)quinoline (3e);
5-fluoro-8-(3-(triisopropylsilyl)prop-2-ynyl)quinoline (3f);
5-bromo-8-(3-(triisopropylsilyl)prop-2-ynyl)quinoline (3g);
5-(trifluoromethyl)-8-(3-(triisopropylsilyl)prop-2-ynyl)quinoline (3h);
5-nitro-8-(3-(triisopropylsilyl)prop-2-ynyl)quinoline (3i);
7-methyl-8-(3-(triisopropylsilyl)prop-2-ynyl)quinoline (3j);
7-fluoro-8-(3-(triisopropylsilyl)prop-2-ynyl)quinoline (3k);
7-chloro-8-(3-(triisopropylsilyl)prop-2-ynyl)quinoline (3l);
6-methyl-8-(3-(triisopropylsilyl)prop-2-ynyl)quinoline (3m);
6-chloro-8-(3-(triisopropylsilyl)prop-2-ynyl)quinoline (3n);
4-chloro-8-(3-(triisopropylsilyl)prop-2-ynyl)quinoline (3o), and
ethyl 4-chloro-8-(3-(triisopropylsilyl)prop-2-ynyl)quinoline-3-carboxylate (3p);
8-(prop-2-yn-1-yl)quinoline. (4a).

The present invention provides a ligand-enabled palladium-catalyzed process for preparation of N-Heterocyclic compounds of Formula A via C—H alkynylation (sp$^3$-sp carbon-carbon bond-forming reaction) of 8-methylquinolines (1a-1p) with alkynyl halides (2) and the said process comprising the steps of:
a. stirring the reaction mixture of alkynyl halide (2), 8-methylquinolines (1a-1p), Palladium-complex, ligand, oxidant, and solvent for the period in the range of 2 to 12 hrs at temperature in the range of 60° C. to 140° C. to afford alkynylated product 3a-p of formula A (wherein $R^2$ is TIPS);
b. adding Tetra-n-butylammonium fluoride (TBAF) in THF to the alkynylated product of step (a) and diluting the mixture with tetrahydrofurane (THF) followed by stirring the reaction mixture at room temperature in the range of 20 to 30° C. for a period in the range of 1 to 2 hr to afford desired desilated product of formula A, where in $R^2$ is H.

Figure 2:
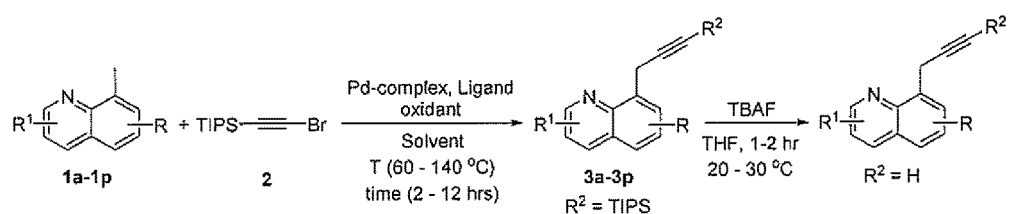
FIG. 2 represents process steps for the preparation on N-heterocyclic compounds of formula A.

The process for the preparation on N-heterocyclic compounds of formula A is shown in FIG. 2.

Ligand used in step (a) is selected from the group consisting of 1,10-phenonthroline, 4-4dimethoxy-2,2-bipyridine, 4,4'-dimethyl-2,2'-dipyridyl, 2,6-Pyridinedicarboxylic acid, Chelidamic acid, 2,2'-Bipyridyl, 3,4,7,8-Tetramethyl-1,10-phenanthroline, 4,7-Dimethoxy-1,10-phenanthroline, L-Isoleucine, 2,6-Pyridinedimethanol, 4-Hydroxy-2,6-Pyridinedicarboxylic acid, 2-Picolinic acid, 2,6-Lutidine, 2,4,6-Trimethylpyridine, 2,6-Di-tert-butylpyridine, 2-Methylpyridine.

Oxidant used in step (a) is selected from the group consisting of potassium persulfate ($K_2S_2O_8$), Oxygen ($O_2$), Copper(II) acetate [$Cu(OAc)_2$], Copper (II) triflate [$Cu(OTf)_2$], manganese(III) acetate [$Mn(OAc)_3.2H_2O$], sodium periodate ($NaIO_4$), N-Methylmorpholine N-oxide (NMO), 1,4-Benzoquinone (BQ), (Diacetoxyiodo)benzene, silver carbonate, silver acetate and silver oxide ($Ag_2O$).

Pd-catalysts used in step (a) is selected from complexes C1-C4, $PdCl_2$, $Pd(ferrocene)(OAc)_2$, $Pd(CH_3CN)_2(Cl)_2$, $Pd(PPh_3)_2(Cl)_2$, $Pd(PhCN)_2(Cl)_2$, $Pd_2(dba)_3$, $Pd(acac)_2$, $Pd(TFA)_2$, and [1,2-Bis(diphenylphosphino)ethane]dichloropalladium(II).

Step (a) is carried out under argon or nitrogen atmosphere.

Alkynyl halide used in step (a) is (bromoethynyl)triisopropylsilane.

Solvent used in step (a) is selected from the group consisting of arenes, toluene, o-xylene, chlorobenzene (PhCl), 1,2-dichloroethane (DCE), Dimethylformamide (DMF), Dimethyl sulfoxide (DMSO), Dimethylacetamide (DMA), Dioxane, tetrahydrofuran (THF) and trifluoroethanol ($CF_3CH_2OH$).

Representative compound of formula 1a-1p are as follows:
8-methylquinoline (1a);
5-methoxy-8-methylquinoline (1b);
N,N,8-trimethylquinolin-5-amine (1c);
5,8-dimethylquinoline (1d);
(E)-8-methyl-5-styrylquinoline (1e),
5-fluoro-8-methylquinoline (1f),
5-bromo-8-methylquinoline (1g);
8-methyl-5-(trifluoromethyl)quinoline (1h);
8-methyl-5-nitroquinoline (1i);
7,8-dimethylquinoline (1j);
7-fluoro-8-methylquinoline (1k);
7-chloro-8-methylquinoline (1l);
6,8-dimethylquinoline (1m);
6-chloro-8-methylquinoline (1n);
4-chloro-8-methylquinoline (1o), and
ethyl 4-chloro-8-methylquinoline-3-carboxylate (1p).

These terminal alkynes of formula A ($R^2$=H) obtained from step (b) are versatile precursor for the 'click reaction'.

Figure 3:
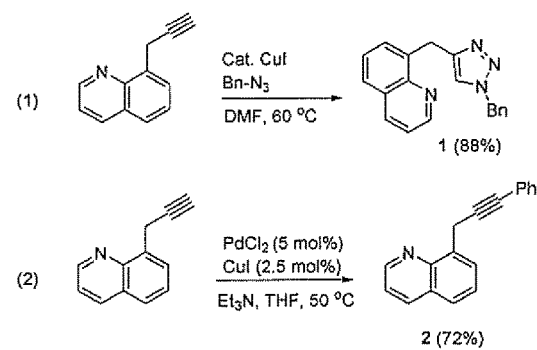
FIG. 3 represents process steps for the preparation on compound of formula 1 and 2 from N-heterocyclic compounds of formula A.

A heterocyclic compound (1) is prepared via copper-catalyzed 'click reaction' as mentioned in FIG. 3. The Compound 1 may be used a potential bidentate ligand in transition-metal catalyzed organic transformations.

Subsequently, the terminal alkynyl moiety of formula A may be easily converted to a phenyl group to yield 2 as mentioned in FIG. 3 in 72% yield through the Sila-Sonogashira coupling reaction, which means other aryl substituents could be similarly introduced. Thus the terminal alkynyl group can be effectively used for making internal alkynes. The unique physical properties of internal alkynes (rigid structure and conjugating π system) make them an attractive functional group for unsaturated molecular scaffolds.

EXAMPLES

The following examples are given by way of illustration and therefore should not be construed to limit the scope of the invention.

Example 1: Synthesis of the Palladium Complexes a) (1,10-phenanthroline)-palladium(II) acetate (C1)

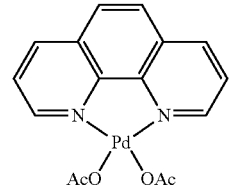

Palladium acetate (56 mg, 0.25 mmol) and 1,10-phenanthroline (Phen) (45 mg, 0.25 mmol) were dissolved in 3.0 mL and 1.0 mL of acetone with stirring, respectively. Then the palladium acetate solution was added dropwise to the 1,10-phenanthroline solution with stirring, forming a yellow precipitate, and the mixture was kept stirring for 2 h at room temperature (30° C.). The precipitate was separated by centrifugation, dried at 60° C. under vacuum for 8 h to yield (Phen)Pd(OAc)₂ C1 as a yellow solid, 98 mg, 97% yield.

Yield=97%. Yellow Solid. $^1$H NMR (CDCl₃, 500 MHz) δ 2.21 (s, 6H), 7.78-7.81 (q, J=5.4 Hz, 2H), 7.96 (s, 2H), 8.51-8.52 (d, J=4.2 Hz, 2H), 8.61-8.62 (d, J=8.2 Hz, 1H). $^{13}$C NMR (CDCl₃, 500 MHz) δ 23.36, 125.19, 127.19, 129.65, 138.80, 146.34, 150.52, 178.63.

b) (2,9-Dimethyl-1,10-phenanthroline)-palladium(II) acetate (C2)

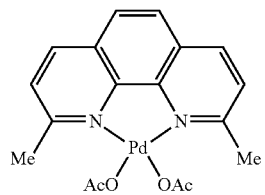

To a 100-ml round-bottom flask with stir bar was added neocuproine (0.600 g, 2.88 mmol), palladium(II) acetate (0.588 g, 2.62 mmol), and acetone (55 mL), and the reaction mixture was stirred overnight (13 hrs). The yellow precipitate was isolated by vacuum filtration, rinsed with acetone, and dried under vacuum to afford 0.87 g of (neocuproine)Pd(OAc)₂ C2 (77% yield).

c) ((2,9-Dimethyl-4,7-diphenyl-1,10-phenanthroline)-palladium(II) acetate (C3)

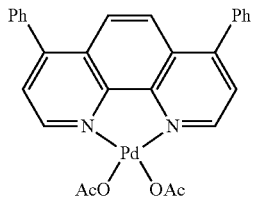

Yield=96%. Yellow Solid. ¹H NMR (CDCl₃, 500 MHz) δ 2.03 (s, 6H), 2.99 (s, 6H), 7.43 (s, 2H), 7.46-7.48 (m, 4H), 7.55-7.57 (m, 6H), 7.80 (s, 2H). ¹³C NMR (CDCl₃, 500 MHz) δ 22.90, 24.70, 124.33, 126.49, 126.81, 129.05, 129.23, 129.71, 135.37, 148.23, 150.86, 164.68, 178.45.

d) (4,7-diphenyl-1,10-phenanthroline)-palladium(II) acetate (C4)

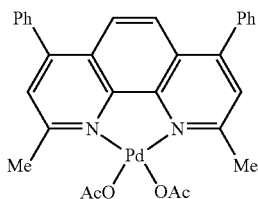

A solution of palladium(II)acetate (449 mg, 2 mmol) in 10 mL of freshly distilled dichloromethane is stirred under argon and bathocuproine (722 mg, 2 mmol) is added in one portion. The resulting solution is stirred under argon at room temperature for 3 hours before the solvent is reduced to a volume of approximately 2 mL. Absolute diethyl ether is added until precipitation occurs and the solution is allowed to stand for 2 hours. The precipitated material is filtered and dried under vacuum to give (bc)Pd(OAc)₂ C4 as a light yellow solid (1.123 g, 1.92 mmol, 96% yield).

Yield=96%. Yellow Solid. ¹H NMR (CDCl₃, 500 MHz) δ 2.21 (s, 6H), 7.51-7.52 (m, 4H), 7.59-7.60 (m, 6H), 7.74-7.76 (d, J=5.4 Hz, 2H), 7.99 (s, 2H), 8.67-8.69 (d, J=5.19 Hz, 2H).

¹³C NMR (CDCl₃, 500 MHz) δ 23.40, 125.25, 125.37, 128.10, 129.24, 129.39, 130.09, 135.05, 147.32, 149.97, 151.76, 178.59.

Example 2: General Procedure for the Direct C(Sp³)-H Alkynylation of N-Heterocycles

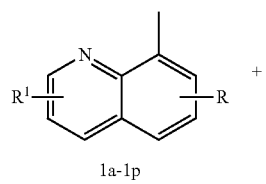

1a-1p

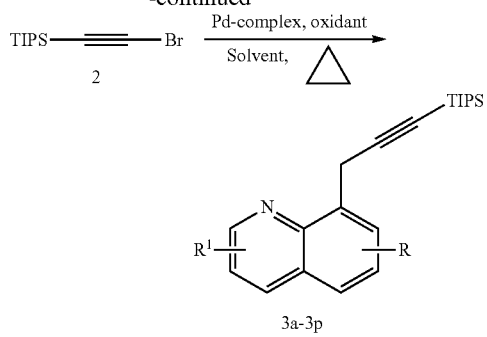

3a-3p

To an oven-dried 15 mL schlenk tube, 8-Methylquinolines (1a-1p) (72 mg, 0.5 mmol), (bromoethynyl)triisopropylsilane 2 (196 mg, 0.75 mmol), 1,10 phenothroline (15 mol % 14 mg, 0.075 mmol), Pd(OAc)₂ (10 mol % 11 mg, 0.05 mmol), Cu(OAc)₂ (91 mg, 0.5 mmol), and DCE (1,2-dichloroethane) (2 mL) were added under a gentle stream of argon. The mixture was stirred for 15 hrs at 110° C. (bath temperature) under open-air. After cooling to room temperature (20 to 30° C.), the mixture was filtered through a celite pad and concentrated in vacuo. The residue was subjected to column chromatography on silica gel (eluent: petroleum ether/ethyl acetate=4/1) to afford the desired alkynylated product (3a-3p) (66 mg, 41%) as a yellow oil.

a) 8-(3-(triisopropylsilyl)prop-2-ynyl)quinoline (3a)

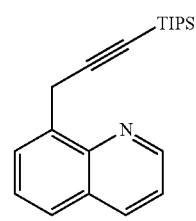

Isolated yield: 9.4 mg (66%). ¹H NMR (CDCl₃, 200 MHz) δ 1.13 (s, 21H), 4.40 (s, 2H), 7.39-7.45 (dd, J=8.2 Hz, 1H), 7.52-7.60 (t, J=7.0 Hz, 1H), 7.71-7.76 (d, J=7.7 Hz, 1H), 8.06-8.11 (dd, J=7.0 Hz, 1H), 8.14-8.19 (dd, J=8.3 Hz, 1H), 8.90-8.94 (dd, J=4.1 Hz, 1H). ¹³C NMR (CDCl₃, 500 MHz) δ 11.38, 18.69, 22.17, 83.56, 106.23, 121.04, 126.42, 126.54, 127.89, 128.18, 135.39, 136.20, 143.03, 149.30. HRMS Calcd for $C_{21}H_{30}NSi$ [M+H]⁺: 324.2148; Found: 324.2142.

b) 5-methoxy-8-(3-(triisopropylsilyl)prop-2-ynyl)quinoline (3b)

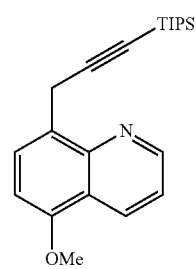

Isolated yield: 13.8 mg (80%). ¹H NMR (CDCl₃, 500 MHz) δ 1.13 (s, 21H), 4.01 (s, 3H), 4.29 (s, 2H), 6.87-6.89 (d, J=7.9 Hz, 1H), 7.38-7.41 (dd, J=8.5 Hz, 1H), 7.95-7.96 (d, J=7.9 Hz, 1H), 8.57-8.59 (dd, J=8.5 Hz, 1H), 8.90-8.91 (d, J=4.2 Hz, 1H). ¹³C NMR (CDCl₃, 500 MHz) δ 11.39, 18.71, 21.69, 55.66, 83.16, 103.91, 106.74, 120.10, 120.60, 126.88, 127.84, 103.81, 146.46, 149.58, 154.03. HRMS Calcd for C$_{22}$H$_{32}$NOSi [M+H]$^+$: 354.2253; Found: 354.2248.

c) N,N-dimethyl-8-(3-(triisopropylsilyl)prop-2-ynyl)quinolin-5-amine (3c)

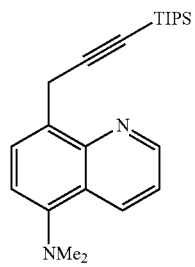

Isolated yield: 15.43 mg (83%). $^1$H NMR (CDCl$_3$, 500 MHz) δ 1.13 (s, 21H), 2.89 (s, 6H), 4.31 (s, 2H), 7.13-7.14 (d, J=7.6 Hz, 1H), 7.27 (s, 1H), 7.40-7.41 (d, J=4.5 Hz, 1H), 7.96-7.97 (d, J=7.6 Hz, 1H), 8.56-8.57 (d, J=8.2 Hz, 2H), 8.88 (s, 1H). $^{13}$C NMR (CDCl$_3$, 500 MHz) δ 11.40, 18.71, 21.94, 45.38, 83.25, 106.66, 114.21, 119.94, 123.72, 127.88, 129.44, 132.81, 146.99, 148.91, 149.80. HRMS Calcd for C$_{23}$H$_{35}$N$_2$Si [M+H]$^+$: 367.2570; Found: 367.2564.

d) 5-methyl-8-(3-(triisopropylsilyl)prop-2-ynyl)quinoline (3d)

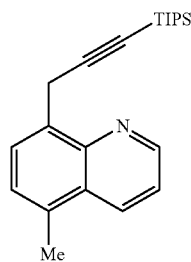

Isolated yield: 11.2 mg (71%). $^1$H NMR (CDCl$_3$, 500 MHz) δ 1.13 (s, 21H), 2.68 (s, 3H), 4.36 (s, 2H), 7.39-7.40 (d, J=7.3 Hz, 1H), 7.44-7.46 (dd, J=4.2 Hz, 1H), 7.95-7.96 (d, J=7.0 Hz, 1H), 8.32-8.34 (dd, J=8.5 Hz, 1H), 8.92-8.92 (d, J=4.2 Hz, 1H). $^{13}$C NMR (CDCl$_3$, 500 MHz) δ 11.38, 18.69, 18.52, 18.69, 83.31, 106.55, 120.60, 126.84, 127.37, 127.83, 132.62, 133.06, 133.28, 146.25, 148.77. HRMS Calcd for C$_{22}$H$_{32}$NSi [M+H]$^+$: 338.2304; Found: 338.2299.

e) (E)-5-styryl-8-(3-(triisopropylsilyl)prop-2-ynyl)quinoline (3e)

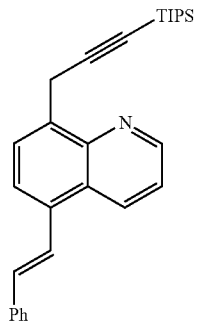

Isolated yield: 18.6 mg (76%). $^1$H NMR (CDCl$_3$, 500 MHz) δ 1.15 (s, 21H), 4.41 (s, 2H), 7.18-7.21 (d, J=16.1 Hz, 1H), 7.31-7.34 (t, J=7.3 Hz, 1H), 7.41-7.44 (t, J=7.6 Hz, 2H), 7.46-7.48 (q, J=3.9 Hz, 1H), 7.60-7.62 (d, J=7.6 Hz, 2H), 7.78-7.81 (d, J=16.1 Hz, 1H), 7.84-7.85 (d, J=7.6 Hz, 1H), 8.10-8.11 (d, J=7.6 Hz, 1H), 8.56-8.58 (dd, J=8.5 Hz, 1H), 8.94-8.95 (dd, J=3.9 Hz, 1H). $^{13}$C NMR (CDCl$_3$, 500 MHz) δ 11.37, 18.71, 22.14, 83.64, 106.20, 120.85, 123.68, 124.21, 126.15, 126.67, 127.99, 128.03, 128.79, 132.28, 132.29, 133.95, 135.03, 127.27, 146.10, 129.11. HRMS Calcd for C$_{29}$H$_{36}$NSi [M+H]$^+$: 426.2617; Found: 426.2612.

f) 5-fluoro-8-(3-(triisopropylsilyl)prop-2-ynyl)quinoline (3f)

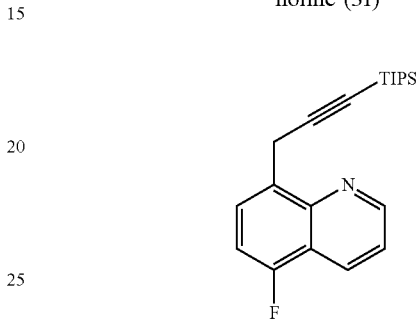

Isolated yield: 9.5 mg (59%). $^1$H NMR (CDCl$_3$, 500 MHz) δ 1.13 (s, 21H), 4.32 (s, 2H), 7.21-7.24 (t, J=8.2 Hz, 1H), 7.46-7.49 (q, J=3.9 Hz, 1H), 7.97-8.00 (t, J=6.7 Hz, 1H), 8.42-8.44 (dd, J=8.2 Hz, 1H), 8.94-8.96 (dd, J=4.2 Hz, 1H). $^{13}$C NMR (CDCl$_3$, 500 MHz) δ 11.36, 18.67, 21.86, 83.74, 105.95, 109.63, 109.78, 118.69, 118.82, 121.06, 127.49, 127.56, 129.41, 129.44, 131.22, 146.18, 150.08, 155.77, 157.79. HRMS Calcd for C$_{21}$H$_{29}$NSi [M+H]$^+$: 342.2053; Found: 342.2048.

g) 5-bromo-8-(3-(triisopropylsilyl)prop-2-ynyl)quinoline (3g)

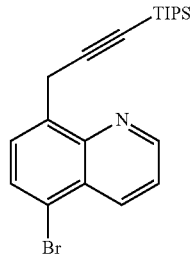

Isolated yield: 13.4 mg (61%). $^1$H NMR (CDCl$_3$, 500 MHz) δ 1.13 (s, 21H), 4.34 (s, 2H), 7.51-7.53 (dd, J=4.2 Hz, 1H), 7.84-7.86 (d, J=7.3 Hz, 1H), 7.93-7.95 (d, J=7.9 Hz, 1H), 8.53-8.58 (d, J=8.5 Hz, 1H), 8.92-8.93 (d, J=3.6 Hz, 1H). $^{13}$C NMR (CDCl$_3$, 500 MHz) δ 11.32, 18.67, 22.16, 84.03, 105.55, 120.25, 122.14, 127.17, 128.55, 130.14, 135.65, 146.58, 149.29, 149.85; HRMS Calcd for C$_{21}$H$_{29}$BrNSi [M+H]$^+$: 402.1253; Found: 402.1247.

h) 5-(trifluoromethyl)-8-(3-(triisopropylsilyl)prop-2-ynyl)quinoline (3h)

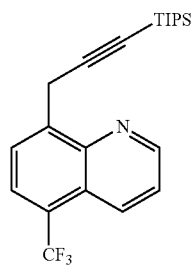

Isolated yield: 10.60 mg (48%). $^1$H NMR (CDCl$_3$, 500 MHz) δ 1.14 (s, 21H), 4.44 (s, 2H), 7.54-7.57 (dd, J=8.8 Hz, 1H), 7.95-7.96 (dd, J=7.6 Hz, 1H), 8.13-8.14 (d, J=7.3 Hz, 1H), 8.50-8.52 (d, J=8.5 Hz, 1H), 8.99-9.00 (d, J=4.2 Hz, 1H). $^{13}$C NMR (CDCl$_3$, 500 MHz) δ 11.34, 18.68, 22.74, 84.55, 105.09, 122.22, 122.67, 123.15, 124.03, 125.07, 125.03, 126.50, 128.76, 132.27, 140.76, 146.03, 149.84, 150.57. HRMS Calcd for C$_{22}$H$_{29}$F$_3$NSi [M+H]$^+$: 392.2021; Found: 392.2016.

i) 5-nitro-8-(3-(triisopropylsilyl)prop-2-ynyl)quinoline (3i)

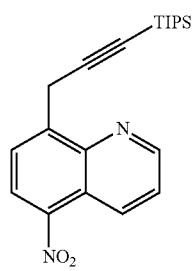

Isolated yield: 9.8 mg (52%). $^1$H NMR (CDCl$_3$, 500 MHz) δ 1.14 (s, 21H), 4.47 (s, 2H), 7.66-7.68 (dd, J=8.8 Hz, 1H), 8.18-8.20 (d, J=7.6 Hz, 1H), 8.43-8.44 (d, J=7.9 Hz, 1H), 9.01-9.03 (dd, J=3.9 Hz, 1H), 9.05-9.07 (dd, J=8.8 Hz, 1H). $^{13}$C NMR (CDCl$_3$, 500 MHz) δ 11.31, 16.67, 23.20, 85.17, 104.39, 120.83, 123.86, 124.69, 126.35, 132.25, 143.98, 144.36, 150.36, 158.90. HRMS Calcd for C$_{21}$H$_{29}$N$_2$O$_2$Si [M+H]$^+$: 369.1998; Found: 369.1996.

j) 7-methyl-8-(3-(triisopropylsilyl)prop-2-ynyl)quinoline (3j)

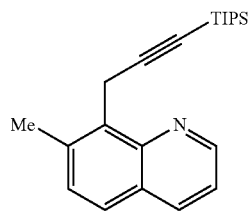

Isolated yield: 12.3 mg (78%). $^1$H NMR (CDCl$_3$, 500 MHz) δ 0.98 (s, 21H), 2.69 (s, 3H), 4.42 (s, 2H), 7.34-7.35 (d, J=4.2 Hz, 1H), 7.40-7.41 (q, J=8.2 Hz, 1H), 7.64-7.65 (d, J=8.2 Hz, 1H), 8.09-8.11 (dd, J=8.2 Hz, 1H), 8.93-8.94 (d, J=4.2 Hz, 1H). $^{13}$C NMR (CDCl$_3$, 500 MHz) δ 11.28, 17.88, 18.56, 20.33, 79.90, 106.68, 120.04, 126.00, 126.67, 129.77, 133.36, 135.95, 137.96, 146.13, 149.46. HRMS Calcd for C$_{22}$H$_{32}$NSi [M+H]$^+$: 338.2304; Found: 338.2299.

k) 7-fluoro-8-(3-(triisopropylsilyl)prop-2-ynyl)quinoline (3k)

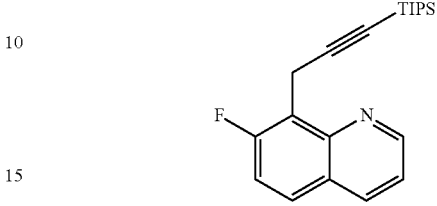

Isolated yield: 13.0 mg (81%). $^1$H NMR (CDCl$_3$, 500 MHz) δ 0.98 (s, 21H), 4.29 (s, 2H), 7.34-7.36 (d, J=8.8 Hz, 1H), 7.38-7.40 (q, J=4.2 Hz, 1H), 7.72-7.75 (q, J=6.1 Hz, 1H), 8.13-8.15 (dd, J=8.2 Hz, 1H), 8.97-8.98 (dd, J=4.2 Hz, 1H). $^{13}$C NMR (CDCl$_3$, 500 MHz) δ 11.25, 18.50, 14.70, 80.03, 105.95, 116.88, 117.07, 120.20, 120.67, 120.79, 125.30, 127.96, 128.04, 136.06, 146.87, 146.93, 150.42, 159.61, 161.59. HRMS Calcd for C$_{21}$H$_{29}$NFSi [M+H]$^+$: 342.2053; Found: 342.2048.

l) 7-chloro-8-(3-(triisopropylsilyl)prop-2-ynyl)quinoline (3l)

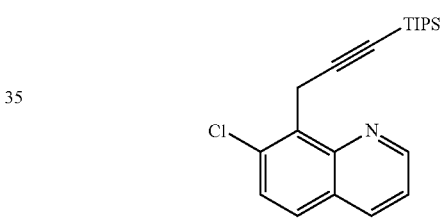

Isolated yield: 14.9 mg (84%). $^1$H NMR (CDCl$_3$, 500 MHz) δ 0.97 (s, 21H), 4.46 (s, 2H), 7.41-7.43 (q, J=4.2 Hz, 1H), 7.55-7.56 (d, J=8.8 Hz, 1H), 7.67-7.69 (d, J=8.8 Hz, 1H), 8.12-8.14 (dd, J=8.2 Hz, 1H), 8.97-8.99 (d, J=4.2 Hz, 1H). $^{13}$C NMR (CDCl$_3$, 500 MHz) δ 11.24, 18.52, 19.26, 80.45, 105.47, 121.01, 126.88, 127.34, 128.20, 133.93, 135.07, 136.06, 146.61, 150.38; HRMS Calcd for C$_{21}$H$_{29}$NClSi [M+H]$^+$: 358.1758; Found: 358.1752.

m) 6-methyl-8-(3-(triisopropylsilyl)prop-2-ynyl)quinoline (3m)

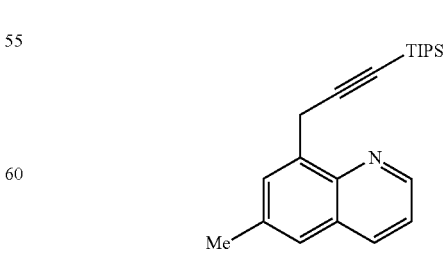

Isolated yield: 11.0 mg (70%). $^1$H NMR (CDCl$_3$, 500 MHz) δ 1.15 (s, 21H), 2.54 (s, 3H), 4.36 (s, 2H), 7.36-7.39 (q, J=4.2 Hz, 1H), 7.49 (s, 1H), 7.97 (s, 1H), 8.05-8.07 (dd, J=8.2 Hz, 1H), 8.84-8.85 (d, J=4.2 Hz, 1H). $^{13}$C NMR (CDCl$_3$, 500 MHz) δ 11.39, 18.69, 21.65, 22.08, 83.70, 106.39, 121.04, 125.23, 128.14, 130.70, 134.82, 135.51, 136.16, 144.67, 148.42. HRMS Calcd for C$_{22}$H$_{32}$NSi [M+H]$^+$: 338.2304; Found: 338.2299.

n) 6-chloro-8-(3-(triisopropylsilyl)prop-2-ynyl)quinoline (3n)

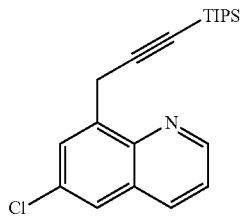

Isolated yield: 11.7 mg (66%). $^1$H NMR (CDCl$_3$, 500 MHz) δ 1.15 (s, 21H), 4.35 (s, 2H), 7.42-7.44 (q, J=4.2 Hz, 1H), 7.70 (d, J=2.4 Hz, 1H), 8.05-8.07 (m, 2H), 8.88-8.90 (dd, J=8.2 Hz, 1H); $^{13}$C NMR (CDCl$_3$, 500 MHz) δ 11.34, 18.68, 22.16, 84.66, 105.19, 121.92, 124.99, 128.64, 129.36, 132.37, 135.29, 137.74, 144.45, 149.42; HRMS Calcd for C$_{21}$H$_{29}$NClSi [M+H]$^+$: 358.1758; Found: 358.1752.

o) 4-chloro-8-(3-(triisopropylsilyl)prop-2-ynyl)quinoline (3o)

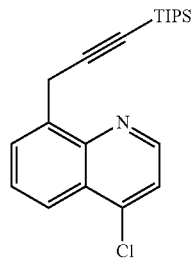

Isolated yield: 14.3 mg (81%). $^1$H NMR (CDCl$_3$, 500 MHz) δ 1.13 (s, 21H), 4.39 (s, 2H), 7.50-7.51 (d, J=4.8 Hz, 1H), 7.64-7.67 (t, J=7.9 Hz, 1H), 8.13-8.17 (t, J=9.1 Hz, 2H), 8.76-8.77 (t, J=4.5 Hz, 1H). $^{13}$C NMR (CDCl$_3$, 500 MHz) δ 11.35, 18.68, 22.47, 83.86, 105.84, 121.25, 122.82, 126.23, 127.39, 129.14, 135.96, 142.76, 146.89, 148.63. HRMS Calcd for C$_{21}$H$_{29}$NClSi [M+H]$^+$: 358.1758; Found: 358.1572.

p) ethyl 4-chloro-8-(3-(triisopropylsilyl)prop-2-ynyl)quinoline-3-carboxylate (3p)

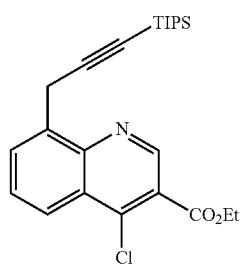

Isolated yield: 18.4 mg (74%). $^1$H NMR (CDCl$_3$, 500 MHz) δ 1.13 (s, 21H), 1.46-1.49 (t, J=7.0 Hz, 3H), 4.39 (s, 2H), 4.50-4.52 (q, J=7.0 Hz, 2H), 7.70-7.73 (t, J=7.9 Hz, 1H), 8.19-8.21 (d, J=6.7 Hz, 1H), 8.33-8.35 (d, J=8.5 Hz, 1H), 9.20 (s, 1H). $^{13}$C NMR (CDCl$_3$, 500 MHz) δ 11.35, 14.23, 18.68, 22.41, 62.05, 84.20, 105.57, 122.98, 124.09, 125.98, 128.16, 130.69, 136.20, 143.51, 147.30, 148.95, 164.65; HRMS Calcd for C$_{24}$H$_{31}$NClO$_2$Si [M−H]$^+$: 428.1813; Found: 428.1807.

Example 3: Synthesis of 8-(prop-2-yn-1-yl)quinoline (4a)

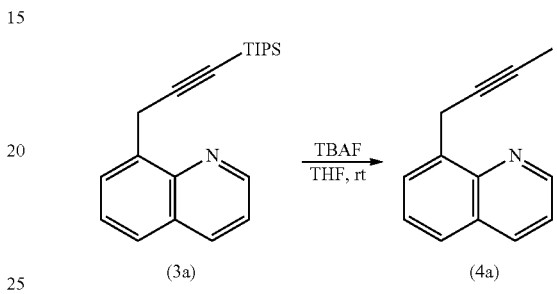

To an oven-dried 10 mL of two-necked flask, 8-(3-(triisopropylsilyl)prop-2-ynyl)quinoline 3a (65 mg, 0.20 mmol) and 1.0 M solution of Tetra-n-butylammonium fluoride (TBAF) in THF (0.25 mL, 0.25 mmol) were added and the mixture was diluted with tetrahydrofuran (THF) (4 mL) under argon atmosphere. The reaction mixture was allowed to stir at room temperature. After 1 h, the reaction mixture was concentrated under vacuum to afford the crude product. The GC and GC-MS showed almost complete conversion and 99% purity of the desired desilated product 4a.

Example 4: Optimization of Reaction Conditions

The reaction conditions are optimized by performing extensive screening of Pd sources, mol % of catalyst, ligands, oxidants, solvent, temperature, and time to obtain the optimum yield of 3a. After extensive screening, toluene is found to be the optimal solvent as it suppressed the homocoupling of 2 and a combination of Pd(OAc)$_2$ and neocuproine (nc) are found to be more appropriate for this transformation and increased the yield (up to 49%) under standard conditions. It is observed that, by using the pre-formed neocuproine palladium complex [(nc)Pd(OAc)$_2$] C2, the yield of 3a is increased to 75%. A well-defined bathocuproine derived Pd(II)-complex C4 also showed comparable reactivity and yielded 3a in 67%. However, the reaction did not proceed in the absence of Cu(OAc)$_2$.

The present C(sp$^3$)-H alkynylation proceeded at 80° C. in good to excellent yields with a variety of electronically diverse substrates. In all cases, a well-defined palladium complex [(nc)Pd(OAc)$_2$] (10 mol %), and oxidant Cu(OAc)$_2$ (2 equiv) are used to achieve excellent yields. From the data, it is observed that the following trends in the C(sp$^3$)-H alkynylation reaction:
  i. Different substituents on the quinoline moiety are compatible with the alkynylation Electron-donating groups proceeded smoothly to provide corresponding C(sp$^3$)-alkynylated products 3b, 3c, and 3e in 80%, 83% and 76% isolated yields respectively, wherein electron-withdrawing groups were found to decrease the yields (48% of 3h and 52% of 3i respectively).

ii. It is noteworthy that halide substituents are tolerated (3f-3g, 3k-3l, and 3n-3p), as this is advantageous for further synthetic elaborations with transition-metal catalysis thereby broadening the diversity of the products.

iii. The position of the substituents on the quinoline moiety played a vital role and thus 5-substituted substrates worked slightly better than 6-substituted substrates. In case of 7-substituted 8-methylquinolines (3j-3l) higher yield of alkynylated product (78% of 3j, 81% of 3k, and 84% of 3l) was obtained by using 25 mol % of catalyst. A multisubstituted ethyl 4-chloro-8-methylquinoline-3-carboxylate (3p) also gave desired alkynylated product. In most cases, the unreacted starting materials are recovered.

The present transformation has broad substrate scope, functional group tolerance and proceed efficiently under mild conditions.

1. Screening of Ligand

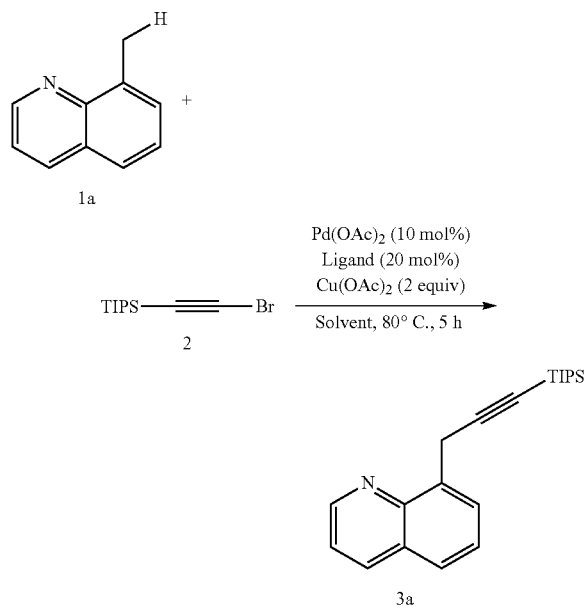

TABLE 1

Screening of ligand

| Entry | Ligand | Yield (%)[a,b] |
|---|---|---|
| 1 | PPh₃ | NR |
| 2 | Xanthphos | NR |
| 3 | dppp | NR |
| 4 | dppb | NR |
| 5 | PCy₃•HBF₄ | NR |
| 6 | Picolinic acid | NR |
| 7 | 4,4 dimethoxy 2-2, bipyridine | 5% |
| 8 | 2,6-pyridinedimethanol | trace |
| 9 | Isoleucine | 4% |
| 10 | BINAP | NR |
| 11 | 2-Amino-4-methoxyphenol | NR |

[a]Reaction conditions: 1a (0.1 mmol), (triisopropylsilyl)ethynyl bromide 2 (0.15 mmol), Pd(OAc)₂ (10 mol %), ligand (20 mol %), Cu(OAc)₂ (2 equiv), toluene (1 mL), 80° C., 5 h.
[b]Analyzed by ¹H NMR analysis using dibromomethane as the internal standard.

2. Screening of Palladium Salts:

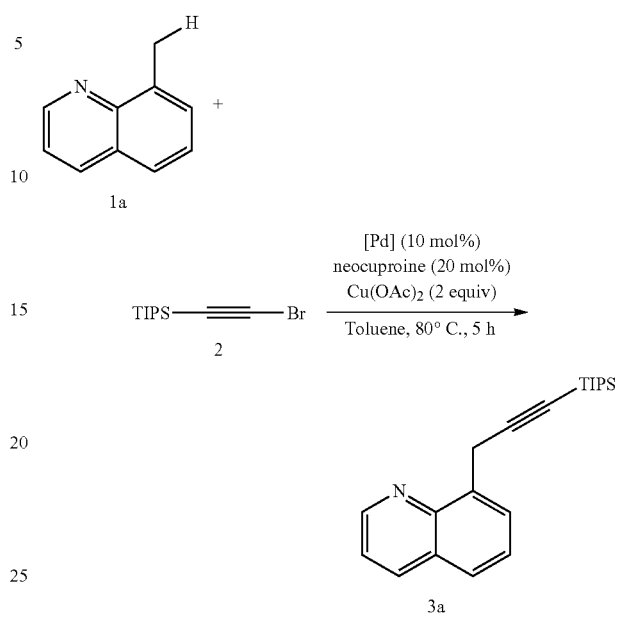

TABLE 2

Screening of Palladium Salts

| Entry | [Pd] | Yield (%)[a,b] |
|---|---|---|
| 1 | PdCl₂ | NR |
| 2 | Pd(ferrocene)(OAc)2 | trace |
| 3 | Pd(CH₃CN)₂(Cl)₂ | 41% |
| 4 | Pd(PPh₃)₂(Cl)₂ | NR |
| 5 | Pd(PhCN)₂(Cl)₂ | 39% |
| 6 | Pd₂(dba)₃ | NR |
| 7 | Pd(acac)₂ | 30% |
| 8 | Pd(TFA)₂ | NR |
| 9 | [1,2-Bis(diphenylphosphino)ethane] dichloropalladium(II) | NR |
| 10 | Pd₂(dba)₃ | NR |

[a]Reaction conditions: 1a (0.1 mmol), (triisopropylsilyl)ethynyl bromide 2 (0.15 mmol), [Pd] (10 mol %), neocuproine (20 mol %), Cu(OAc)₂ (2 equiv), toluene (1 mL), 80° C., 5 h.
[b]The yield was determined by ¹H NMR analysis of the crude product using dibromomethane as the internal standard.

3. Effect of Oxidants

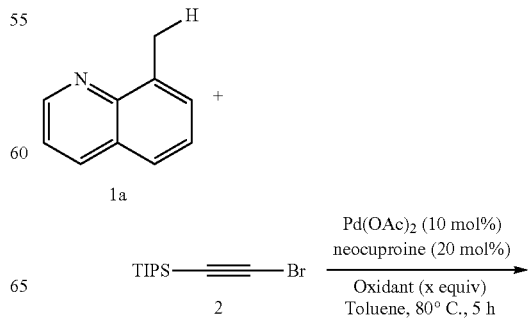

-continued

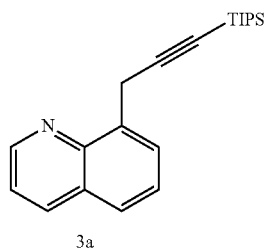

3a

TABLE 3

Effect of Oxidants

| Entry | Oxidant | Equiv. of oxidant (x) | Yield of 3a (%)[a,b] |
|---|---|---|---|
| 1 | $K_2S_2O_8$ | 2 | 10% |
| 2 | $PhI(OAc)_2$ | 2 | 6% |
| 3 | NFSI | 2 | 15% |
| 4 | $Cu(OAc)_2$ | 1 | 31% |
| 5 | TBHP | 1 | NR |
| 6 | $Cu_2O$ | 1 | 10% |
| 7 | $Cu(acac)_2$ | 2 | 8% |
| 8 | $Ag_2CO_3$ | 1 | 12% |
| 9 | $Ag_2O$ | 1 | 10% |
| 10 | AgOAc | 2 | 5% |
| 11 | $Cu(OAc)_2$ | 2 | 42% |
| 12 | $Cu(OAc)_2$ | 3 | 23% |
| 13 | $Cu(OAc)_2$ | 0.5 | 7% |
| 14 | — | — | NR |
| 15 | $O_2$ | 1 atm | NR |
| 16 | Oxone | 1 | trace |
| 17 | $NaNO_3$ | 2 | NR |
| 18 | $Cu(OTf)_2$ | 1 | 8% |
| 19 | p-Benzoquinone | 1 | trace |
| 20 | $V_2O_5$ | 2 | trace |
| 21 | $AgNO_3$ | 1 | NR |

[a]Reaction conditions: 1a (0.1 mmol), (triisopropylsilyl)ethynyl bromide 2 (0.15 mmol), Pd(OAc)₂ (10 mol %), neocuproine (20 mol %), oxidant (x equiv), toluene (1 mL), 80° C., 5 h.
[b]The yield was determined by ¹H NMR analysis of the crude product using dibromomethane as the internal standard.

4. Effect of Solvent

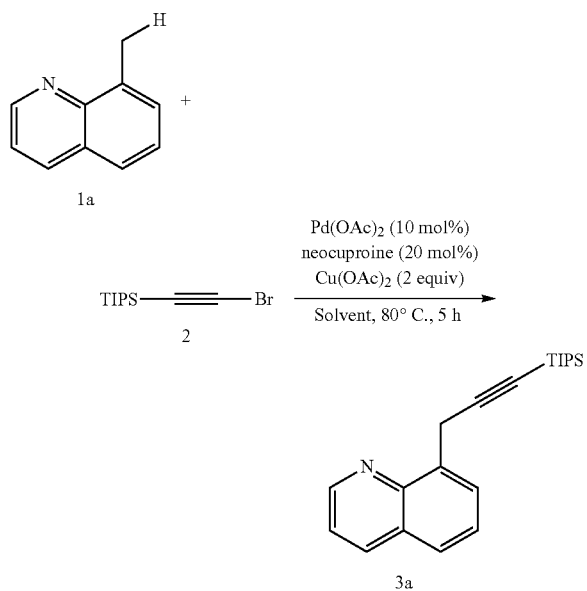

TABLE 4

Effect of Solvent

| Entry | Solvent | Yield of 3a (%)[a,b] |
|---|---|---|
| 1 | Toluene | 42% |
| 2 | DCE | 8% |
| 3 | DMSO | NR |
| 4 | DMF | NR |
| 5 | THF | 12% |
| 6 | 1,4-Dioxane | 10% |
| 7 | Toluene + DMSO (1:1) | NR |
| 8 | m-Xylene | 37% |
| 9 | Acetic acid | trace |
| 10 | $C_6F_6$ | trace |
| 11 | t-Amyl alcohol | NR |
| 12 | $CH_3CN$ | 28% |
| 13 | MeOH | 12% |

[a]Reaction conditions: 1a (0.1 mmol), (triisopropylsilyl)ethynyl bromide 2 (0.15 mmol), Pd(OAc)₂ (10 mol %), neocuproine (20 mol %), Cu(OAc)₂ (2 equiv), solvent (1 mL), 80° C., 5 h.
[b]The yield was determined by ¹H NMR analysis of the crude product using dibromomethane as the internal standard.

5. Effect of Temperature, Reaction Time, and Effect of Mol % of Catalyst (C2)

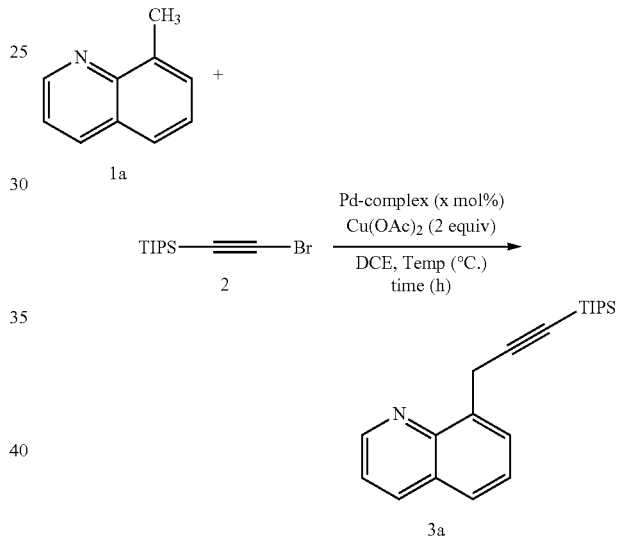

Figure 1B:
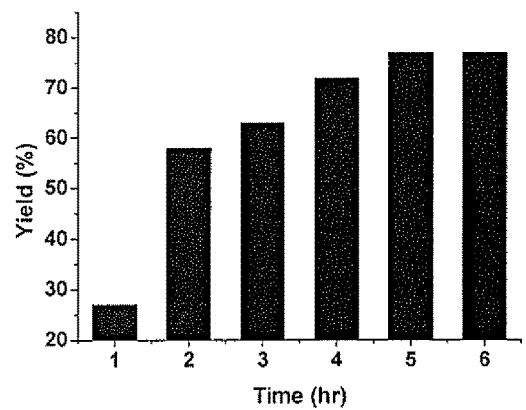
Figure 1C:
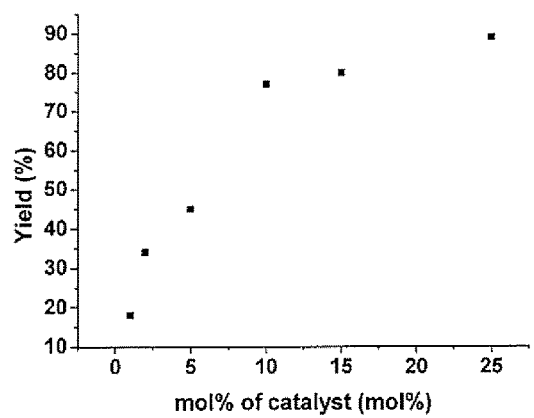
FIG. 1C represents effect of mol % of catalyst (C2).

FIG. 1A-FIG. 1C represent effect of temperature, reaction time, and effect of mol % of catalyst (C2) respectively for the C—H alkynylation of inert C(sp³)-H bonds of 1a.

FIG. 1A represents effect of temperature wherein reaction conditions are as follow: 1a (0.1 mmol), 2 (0.15 mmol), Pd-complex C1-C4 (10 mol %), Cu(OAc)₂ (2 equiv) and toluene (1 mL) in a 10 mL screw-capped viol were heated at T temp. (° C.) for 5 hr. The yield was determined by ¹H NMR analysis of the crude product using dibromomethane as the internal standard).

FIG. 1B represents effect of reaction time wherein reaction conditions are as follow: 1a (0.1 mmol), 2 (0.15 mmol), Pd-complex C1-C4 (10 mol %), Cu(OAc)₂ (2 equiv) and toluene (1 mL) in a 10 mL screw-capped viol were heated at 80° C. for T time (hr). The yield was determined by ¹H NMR analysis of the crude product using dibromomethane as the internal standard).

FIG. 1C represents effect of mol % of catalyst (C2), wherein reaction conditions are as follow: 1a (0.1 mmol), 2 (0.15 mmol), complex C2 (x mol %), Cu(OAc)₂ (2 equiv) and toluene (1 mL) in a 10 mL screw-capped viol were heated at 80° C. for 5 hr. The yield was determined by ¹H NMR analysis of the crude product using dibromomethane as the internal standard).

Advantages of the Invention

1. The Novel compounds of formula A may used for further derivatization in many synthetic transformations (including cycloaddition, metathesis, click reaction etc.) leads to various useful molecules.
2. The compounds of formula A may find applications in synthetic chemistry, material science and they are also a common motif in pharmaceutics.
3. Novel ligand-enabled palladium-catalyzed process for preparation of novel N-Heterocyclic compounds of Formula A via C—H alkynylation of N-heterocycles with alkynyl halides is provided.

The invention claimed is:

1. A heterocyclic compound of formula A

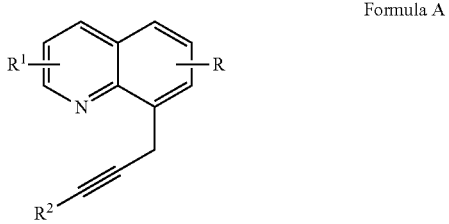

Formula A wherein, $R^1$ is independently selected from the group consisting of hydrogen, alkyl (linear and branched), cycloalkyl, aryl, heterocyclyl, heteroaryl, alkylcycloalkyl, alkylaryl, alkylheterocyclyl, alkylheteroaryl, alkenyl, halogen, triflurometyl, nitro, amide, ester, cyano, alkoxy, alkylamino, arylamino, an inorganic support and a polymeric moiety;

R is selected from the group consisting of H, alkyl (linear, branched), cycloalkyl, aryl, heterocyclyl, heteroaryl, alkylcycloalkyl, alkylaryl, alkylheterocyclyl, alkylheteroaryl, alkenyl, halogen, triflurometyl, nitro, amide, ester, cyano, alkoxy, alkylamino, arylamino, an inorganic support and a polymeric moiety;

$R^2$ is H or the heterocyclic compound is 8-(3-(triisopropylsilyl)prop-2-ynyl)quinoline (3a).

2. The compound as claimed in claim 1, wherein the heterocyclic compound of formula A is 8-(prop-2-yn-1-yl)quinoline (4a).

3. A process for preparation of heterocyclic compound 8-(prop-2-yn-1-yl)quinoline (4a) comprising the steps of:
   a) stirring the reaction mixture of (bromoethynyl) triisopropylsilane (2), 8-methylquinolines (1a), Pd(OAc$_2$)$_2$, 1,10-phenanthroline, Cu(OAc)$_2$, and 1,2-dichloroethane (DCE) as a solvent for 15 hrs at a temperature of 110° C. to afford alkynylated product 8-(3-(triisopropylsilyl)prop-2-ynyl)quinoline (3a);
   b) adding Tetra-n-butylammonium fluoride (TBAF) in THF to the alkynylated product of step (a) and diluting the mixture with tetrahydrofurane (THF) followed by stirring the reaction mixture at room temperature for 1 hr to afford desired desilated product 8-(prop-2-yn-1-yl)quinoline (4a).

4. The process as claimed in claim 3, wherein said process is carried out at argon or nitrogen atmosphere.

* * * * *